United States Patent [19]

Priemer et al.

[11] 4,033,987
[45] July 5, 1977

[54] ISOLATING NAPHTHOQUINONE AND PHTHALIC ANHYDRIDE FROM NAPHTHALENE OXIDATION PRODUCT

[75] Inventors: Joachim Priemer, Odenthal; Norbert Schenk, Leverkusen; Jorg Krekel, Essen; Wulf Schwerdtel, Leverkusen, all of Germany

[73] Assignee: Bayer Aktiengesellschaft, Leverkusen, Germany

[22] Filed: July 16, 1976

[21] Appl. No.: 706,093

[30] Foreign Application Priority Data

July 19, 1975 Germany .................. 2532388

[52] U.S. Cl. .................. 260/346.4; 260/396 R; 260/369
[51] Int. Cl.² .................. C07D 307/89; C07C 49/66
[58] Field of Search ......... 260/396 R, 346.4, 346.7, 260/369

[56] References Cited
FOREIGN PATENTS OR APPLICATIONS 49-135957  12/1974  Japan
49-135956  12/1974  Japan

*Primary Examiner*—Henry R. Jiles
*Assistant Examiner*—Bernard Dentz
*Attorney, Agent, or Firm*—Burgess, Dinklage & Sprung

[57] ABSTRACT

To isolate naphthoquinone and phthalic anhydride from the gas obtained in the gas phase oxidation of naphthalene, the gas product at 250° to 500° C is first quenched with a counter-current liquid stream of naphthalene, naphthoquinone and phthalic anhydride. The liquid is raised to at most 200° C, cooled and partly recycled, the coolant temperature being within 70° C of the temperature of the liquid being cooled. The portion of the quench liquid which is not recycled is the product, viz. a solution of naphthoquinone and phthalic anhydride in naphthalene. The quenched gas is scrubbed with liquid naphthalene and most of the liquid product is cooled and re-cycled, the balance of the liquid product being passed to the quencher. The gas which leaves the scrubber is substantially free from naphthoquinone and phthalic anhydride. The initial gas may have been pre-cooled by evaporative cooling. The surfaces of the quencher, cooler and pipes of the quenching system are preferably of stainless steel or are smoothed either mechanically or by coating with plastic, enamel, ceramic or metal.

15 Claims, 1 Drawing Figure

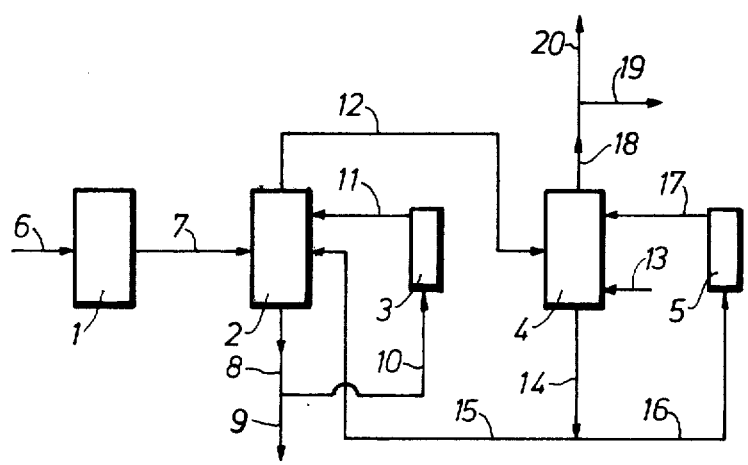

ISOLATING NAPHTHOQUINONE AND PHTHALIC ANHYDRIDE FROM NAPHTHALENE OXIDATION PRODUCT

The present invention relates to a particularly advantageous method of isolating naphthoquinone and phthalic anhydride from the reaction gases of the gas phase oxidation of naphthalene, a liquid mixture which essentially contains naphthalene, naphthoquinone and phthalic anhydride being obtained.

When naphthalene is oxidized in the gas phase, a reaction gas is obtained which generally contains naphthoquinone, phthalic anhydride, napthalene, steam, carbon dioxide, oxygen and inert stubstances. It is difficult to separate naphthoquinone from such a reaction gas since naphthoquinone is a metastable product which during isolation tends to react further and to form tar. Furthermore, due to the simultaneous presence of phthalic anhydride and water or steam, precipitation of phthalic acid can occur. Both the formation of tar and the precipitation of phthalic acid make a continuous isolation of naphthoquinone and phthalic anhydride from the reaction gas more difficult, or prevent such an isolation, since in this case deposits and blockages arise in the apparatus used.

It is known from U.S. Pat. Specification No. 2,938,913 first to cool the reaction gases from the oxidation of naphthalene to temperatures which are slightly above the dew point (about 170°–180° C) and then to take up the gases cooled in this way in an inert high-boiling solvent which is immiscible with water (for example chloronaphthalene). With this procedure, the formation of tars is observed during cooling and, due to the use of foreign solvents, particular technical effort and expenditure on energy are necessary.

According to German Published Specification DOS 2,422,689, cooling of the reaction gases is effected by bringing them into direct contact, in co-current, with liquid naphthalene and thus cooling them rapidly, and while keeping the coolant in the liquid phase, to temperatures below the dew point. The content of oxidation products in the liquid phase must be kept as low as possible because otherwise decomposition of naphthoquinone and the formation of tars occur. Following this cooling, during which naphthoquinone and phthalic anhydride remain partially in the gas phase, the cooled reaction gases and the coolant are again brought into contact with further naphthalene in a collecting device. With this process the total heat withdrawn from the reaction gases is obtained in the form of a warmed naphthalene solution, which is not suitable for recovery of the heat. Furthermore, the entire naphthoquinone passes through a two-stage treatment with naphthalene before it is separated off and this is particularly expensive in respect of apparatus and energy. Furthermore, with this process phthalic anhydride and water or stream are in contact with one another during two stages of working up and this means that the danger of the formation of blockages due to phthalic acid crystallizing out is increased.

The object of the present invention is to provide a process for separating off naphthoquinone and phthalic anhydride, from the gases obtained from the oxidation of naphthalene, in which these disadvantages are avoided.

A process for isolating naphthoquinone and phthalic anhydride from the gases obtained from the oxidation of naphthalene has now been found, which is characterized in that the gases obtained from the oxidation of naphthalene are passed, at a temperature ranging from about 250° to 500° C and under pressure, into a quencher which is operated in counter-current, a liquid which contains naphthalene, naphthoquinone and phthalic anhydride is taken off, at a temperature of less than about 200° C, from the sump of the quencher, part of this liquid is withdrawn from the system and the remaining amount of this liquid is recycled via a cooler to the top of the quencher, the cooler being operated with a liquid coolant which has a temperature which differs from that of the liquid to be cooled by at most about 70° C, a gas, which still contains only small amount of naphthalene, naphthoquinone and phthalic anhydride, is taken off at the top of the quencher at temperatures of less than about 150° C, this gas is washed with naphthalene in a scrubber, naphthalene, which may contain small amounts of naphthoquinone and phthalic anhydride, is taken off at the bottom of the scrubber, a minor proportion of this solution is fed into the quencher and the major proportion of this solution is recycled via a cooler into the scrubber, and a gas which is virtually free from naphthoquinone and phthalic anhydride is taken off at the top of the scrubber.

The reaction gases obtained from a gas phase oxidation of naphthalene carried out in any desired manner are suitable as the feed product for the process according to the invention. Preferably, reaction gases, from the oxidation of naphthalene, which contain a relatively high proportion of naphthoquinone are employed. Such reaction gases can be obtained, for example, by the process of U.S. Pat. Specification No. 2,863,884 (the disclosure or which is incorporated herein by reference), and also by other processes.

The gases obtained from the oxidation of naphthalene generally have a temperature in the range from 250° to 500° C and can be obtained at atmospheric pressure or under pressure. For use in the process according to the invention, the feed gas should have a pressure of, for example, about 2 to 10 bars. Pressures of about 3 to 7 bars are preferred and pressures of about 4 to 6 bars are particularly preferred. The oxidation of naphthalene can be carried out under pressures such that the resulting reaction gases can be introduced without a change in pressure into the process according to the invention.

According to the invention, the gases obtained from the oxidation of naphthalene are fed to a quencher. A quencher is a device in which a stream of gas which is to be cooled is brought into direct contact with the coolant and, therefore, the cooling and condensation process proceeds very rapidly, for example in a few seconds or fractions of a second. A known example of the cooling of reaction gases in quenchers is the cooling of cracked gases (compare Ullmanns Encyclopadie der technischen Chemie (Ullmann's Encyclopaedia of Industrial Chemistry), 4th edition, volume 2, page 416 and volume 8, page 176 et seq.). According to the invention, a quencher which is operated in counter-current is used. There are very diverse design possibilities for quenchers. For example, a quencher which consists of a sump boiler onto which a column section is fitted can be used. In order to improve the contact between the gas and the liquid, the column can contain packing or inserts. Examples of suitable packings and inserts are: drip trays, bubble trap trays, valve trays, sieve trays, expanded metal trays or packing of any desired form. It is also possible to obtain good contact between the gas and the liquid without using packings or inserts. For example, a spray scrubber can be employed for this purpose.

The wall surfaces of the quencher can be heatable. If appropriate, heating is so carried out that the quenched products remain liquid. Preferably, heating is in the temperature range of about 80°-140° C.

The gas to be passed into the quencher can be passed in at any desired point in the lower part of the quencher. Passing the gas into the sump of the quencher is preferred. The gas feed can, for example, be so effected that the gas bubbles through the liquid or that the gas enters above the level of the liquid. The stream of feed gas can also be divided into several partial streams, which are then passed into the quencher at different inlet points, which are preferably staggered at different heights.

The quenching liquid is taken off from the sump of the quencher at a temperature of less than 200° C. The temperature of the quenching liquid which is taken off preferably ranges from about 60° to 150° C and particularly preferentially ranges from about 80 to 120° C. The quenching liquid which is taken off essentially contains naphthalene, napthoquinone and phthalic anhydride.

The liquid taken off at the sump of the quencher is divided into two partial streams. One partial stream, for example about 0.1 to 10%, preferably about 0.3 to 1.5%, of the total stream, is withdrawn from the system. This partial stream which is withdrawn contains the naphthoquinone and phthalic anhydride, isolated by the process according to the invention, in the form of a solution in naphthalene. This process product can be worked up to give pure naphthoquinone and pure phthalic anhydride but it is preferably further used directly, for example for the preparation of anthraquinone by reacting the process product with butadiene to give tetrahydroanthraquinone and subsequently converting this to anthraquinone. Preferably, the amount of process product which is withdrawn from the process corresponds to the amount of naphthoquinone and phthalic anhydride which is introduced into the quencher with the feed gas.

The proportion of the liquid, which is taken off at the sump of the quencher, which is not withdrawn from the system is recycled via a cooler to the top of the quencher. In quenchers which are operated in the customary manner as small as possible an amount of quenching liquid is recycled and the dimensions of the cooler are as small as possible; this is possible only when the temperature difference between the coolant and the recycled quenching liquid is as large as possible. This procedure is not very suitable for the process according to the invention since, when the temperature differences between the coolant and the recycled quenching liquid are large, deposits form in the cooler, which make a continuous procedure more difficult or prevent such a procedure. It has been found that a trouble-free continuous procedure is possible only when the amount of quenching liquid which is recycled and the dimensions of the cooler are such that the temperature difference between the coolant and the recycled quenching liquid is less than 70° C, preferably less than about 50° C. Particularly preferentially, this temperature difference is less than about 20° C. The quenching liquid is preferably passed through the cooler in turbulent flow.

The quenching liquid cooled in this way is returned to the top of the quencher. This liquid can be introduced into the quencher by means of a distribution device for the liquid, for example through a central nozzle or through several individual nozzles. It is also possible for a jet of liquid to impinge on a dispersion cone, producing a distribution of the liquid which describes a cone-like surface. Rotary distributors for liquids can also be employed. The introduction of the liquid into the quencher by means of liquid jets and dispersion cones is preferred.

The amount of quenching liquid which is recycled is such that the temperature of the gases which issue at the top of the quencher is less than about 120° C and that a liquid having the temperatures previously described is obtained at the sump of the quencher.

Materials which can be used for the containers, coolers and tubes of the quenching system are steels, especially stainless steels, for example material 1.4571 according to DIN Standard 17,007. Especially in the case of materials which are not stainless steels it has proved advantageous to use, in the total quenching system, those containers, coolers and tubes in which the surfaces which come into contact with the product have been polished. Polishing can be carried out mechanically, for example by polishing with a polishing paste or a buffing disc. However, the surfaces can also be finished by coating with plastics, enamel, ceramics or metal.

The stream of gas which is taken off at the top of the quencher at a temperature of less than about 150° C, preferably less than 120° C and especially about 100° to 120° C contains the proportions of the feed gas which have not condensed in the quenching system. This stream of gas essentially contains inert substances, carbon dioxide, oxygen, steam and naphthalene vapor as well as small amounts of naphthoquinone and phthalic anhydride. In order to isolate these amounts of naphthoquinone and phthalic anhydride also, as well as to permit problem-free recycling of this gas into the oxidation of naphthalene, this stream of gas is subjected, according to the invention, to a wash with naphthalene. The scrubber used for this purpose can be constructed in any desired manner, for example as a co-current or counter-current scrubber. Preferably, a counter-current scrubber in which the liquid coolant is pumped round through a cooler is used for this wash. The temperature of the wash liquid can generally be in the range from about 60° to 120° C. Preferably, the temperature of the wash liquid is about 80° to 100° C. Any desired naphthalene, including contaminated naphthalene, can be introduced into the scrubber. Preferably, the naphthalene required for the gas phase oxidation is introduced into this scrubber. With this procedure it is possible to use the stream of gas which is taken off at the top of the scrubber and which is virtually free from naphthoquinone and phthalic anhydride, direct as the feed gas in the oxidation of naphthalene. The gas taken off at the top of the naphthalene scrubber has virtually the same temperature as the wash liquid. A dilute solution of naphthoquinone and phthalic anhydride in naphthalene is taken off at the bottom of the naphthalene scrubber. Part of this solution, e.g. about 1 to 40% and preferably about 5 to 15%, is recycled into the first quenching system. The remaining amount of the liquid taken off at the sump is recycled via a cooler to the top of the scrubber.

In a particularly preferred embodiment of the process according to the invention, the gases obtained from the oxidation of naphthalene are not passed directly into the quencher, which is operated in countercurrent, but are pre-cooled before being introduced. If this pre-cooling is carried out, care must be taken that the gases are not cooled to temperatures below about 280° C before they enter into the first quencher. Suitable coolers are any desired known cooling apparatuses. In order reliably to ensure that the temperature is as far as possible constant and uniform over all the cooling surfaces, an evaporative cooler is preferably used. In an evaporative cooler a coolant is brought to the boil by the heat which is removed from the gases obtained from the oxidation of naphthalene, the resulting vapors of the boiling medium are condensed in a further condenser and the condensate is returned to the boiling medium in the pre-cooler. Evaporative cooling thus represents a closed system as far as the boiling medium is concerned. The temperature level of the evaporative cooler can be influenced as desired by the choice of the boiling medium and by the choice of the pressure in the system on the boiling medium side. For example, water or a high-boiling organic liquid can be used as the boiling medium. Another embodiment for pre-cooling consists in using a conventional heat exchanger in which the feed gases for the oxidation of naphthalene are heated by the gases obtained from the oxidation of naphthalene. It is also possible to effect pre-cooling in an air cooler.

An industrial embodiment of the process according to the invention is explained with the aid of the attached drawing which is a schematic flow sheet:

The gases obtained from the oxidation of naphthalene are preferably passed via line 6 to a pre-cooler 1, in which the gases are pre-cooled to temperatures of 280°-300° C. The pre-cooler 1 consists of an evaporative cooler operated with water. The pre-cooled gases are fed via line 7 into the quencher 2. A liquid mixture of naphthalene, phthalic anhydride and naphthoquinone is taken off, at a temperature in the range of 100°-150° C, at the bottom of the quencher 2 via line 8. A relatively small proportion of this liquid mixture is taken off via line 9 and can be used for the further conversion of naphthoquinone to anthraquinone. The major proportion of the liquid mixture 8 taken off at the bottom of the quencher 2 is fed, via line 10 to the cooler 3. This cooler is operated with a liquid coolant which is less than 20° C colder than the mixture in line 10. The liquid cooled in this way is fed via line 11 to the top of the quencher 2. The proportions of the gases supplied via line 7 which have not condensed are taken off at the top of the quencher 2 at temperatures of about 100°-150° C. These gases 12 essentially contain nitrogen, carbon dioxide, oxygen, steam and certain amounts of gaseous naphthalene, as well as small amounts, which depend on the particular vapor pressure, of naphthoquinone and phthalic anhydride, and are passed into a scrubber 4. Fresh naphthalene is fed into this scrubber via line 13. A dilute solution of naphthoquinone and phthalic anhydride in naphthalene is taken off at the bottom of the scrubber 4 via line 14. The major proportion of this solution is recycled via line 16, the cooler 5 and line 17 to the top of the scrubber 4. The smaller proportion of this solution is fed via line 15 into the quencher 2. An off-gas which contains naphthalene and is virtually free from phthalic anhydride and naphthoquinone is taken off at the top of the scrubber 4 via line 18. Some of this gas is recycled via line 19 into the oxidation of naphthalene and the remainder, if appropriate after further purification, is released via line 20 as off-gas. The quencher, the scrubber and the pipes carrying the product can be heated. Heating is effected by means of stream or by means of a heat carrier medium. Twin jacket designs are used for the quencher, the scrubber and the pipes which carry the product. Heating is to temperatures in the range of 80°-140° C.

The process according to the invention has the advantage that it can be carried out continuously virtually trouble-free because deposits and blockages are virtually completely avoided. Moreover, the bulk of the naphthoquinone and phthalic anhydride isolated is subjected to quenching only once. If a pre-cooler is used, part of the heat contained in the gases obtained from the oxidation of naphthalene can be re-used in an economical manner, for example for preheating the gases to be fed into the oxidation of naphthalene.

The liquid mixture which is obtained according to the invention and which essentially contains naphthalene, naphthoquinone and phthalic anhydride can be reacted with butadiene, the naphthoquinone being converted into tetrahydroanthraquinone. Anthraquinone, which is an important intermediate product for the preparation of dyestuffs, is obtainable from tetrahydroanthraquinone by oxidative dehydrogenation. The further processing of the mixture which is produced according to the invention can, for example, be carried out in accordance with the process of German Published Specification DOS 2,245,555.

The process is further described in the following illustrative examples:

EXAMPLE 1

A reaction gas which is obtained from the oxidation of naphthalene and has a temperature of 380° C and a pressure of 5 bars and is of the following composition: 74% by weight of nitrogen, 3% by weight of oxygen, 4% by weight of water, 10% by weight of carbon dioxide, 7% by weight of naphthalene, 1% by weight of naphthoquinone and 1% by weight of phthalic anhydride is fed via line 6 to the pre-cooler 1. The pre-cooler is a tube cooler which consists of 9 tubes with a length of 3.5 m and an internal diameter of 33 mm and which is operated as an evaporative cooler, isododecane serving as the coolant. The gas is cooled to 290° C in the pre-cooler. The gas passes via line 7, which is heated electrically to the same temperature, into the quencher 2. This consists of a sump boiler, which is 0.8 m in diameter and about 1.6 m in height and has a conical base, and a column section which is 0.3 m in diameter and 2.4 in height. The inserts consist of 6 drip trays. The quenching liquid is pumped through the cooler 3 and fed, via a dispersion cone at the top of the column, into the quencher. In the quencher 2, the cooler 3 for the quenching liquid and the pipes 8, 10 and 11, which connect these two apparatuses, all the surfaces which come into contact with the product have been smoothed by coating with a synthetic resin.

The amount of gas which enters the system is 340 cubic meters (S.T.P.) per hour and the amount of quenching liquid is 15 cubic meters per hour. The composition of the quenching liquid is about 77% by weight of naphthalene, 11% by weight of naphthoquinone, 11% by weight of phthalic anhydride, 0.3% by weight of phthalic acid and 0.7% by weight of high-boiling compounds. The sump temperature is 112° C, the temperature of the stream of gas which issues at the top of the quencher is 103° C, the temperature of the liquid sprayed in is also 103° C and the average temperature of the coolant in the cooler 3 is 80° C. The stream of gas 12 containing small amounts of naphthoquinone which have not condensed out is passed into the after-wash 4, which consists of a sump boiler and a column section constructed to the same dimensions as the quencher. The sump temperature here is 96° C and the temperature of the gas at the top is 92° C and the amount of wash liquid pumped round per hour is about 3 m³. The average temperature of the coolant in the cooler 5 is 80° C. The wash liquid is approximately 99% pure naphthalene. The naphthalene required for the oxidation of naphthalene is fed in via the wash 4. Liquid product is passed, via a liquid level regulator, from the after-wash into the quencher. The amount fed to the quencher corresponds to the sum of the feed of fresh naphthalene and condensed residual amounts obtained from the stream of gas. 80 kg/hour of quenching liquid are taken off at the sump of the quencher via line 9.

EXAMPLE 2

A quencher which had the same dimensions as in Example 1 but which contained no inserts in the column section was used. All the parts of the apparatus were manufactured from stainless steel (material 1.4517 according to DIN Shape 17007). The quenching capacity was finely distributed.

300 cubic meters (S.T.P.) per hour of a reaction gas are employed, the gas having a temperature of 340° C, a pressure of 6 bars and the following composition: 79% by weight of nitrogen, 3% by weight of oxygen, 5% by weight of water, 2% by weight of carbon dioxide, 7% by weight of naphthalene, 2% by weight of naphthoquinone and 2% by weight of phthalic anhydride.

The composition of the quenching liquid is: 78% by weight of naphthalene, 10% by weight of naphthoquinone, 11% by weight of phthalic anhydride, 0.3% by weight of phthalic acid and 0.7% by weight of high-boiling compounds.

The temperatures in the quencher are:
Sump temperature 117° C
Temperature at the top 111° C
Average temperature of the coolant 100° C
Temperature of the cooled quenching liquid 110° C.
The temperatures in the scrubber are:
Sump temperature 105° C
Temperature at the top 99° C
Average temperature of the coolant 90° C
Temperature of the cooled washing liquid 100° C.

70 kg/hour of the quenching liquid are taken off via line 9.

The other measures correspond to those in Example 1.

It will be appreciated that the instant specification and examples are set forth by way of illustration and not limitation, and that various modification and changes may be made without departing from the spirit and scope of the present invention.

What is claimed is:

1. A process for isolating naphthoquinone and phthalic anhydride from the gases obtained from the oxidation of naphthalene, comprising passing the gases obtained from the oxidation of naphthalene at a temperature of about 250° to 500° C and under pressure into a quencher, passing into said quencher in counter-current to said gas a liquid which contains naphthalene, naphthoquinone and phthalic anhydride, taking off liquid at a temperature of less than about 200° C from the sump of the quencher, cooling part of this liquid and recycling it to the top of the quencher, cooling being effected with a liquid coolant which has a temperature at most about 70° C below that of the liquid to be cooled, at the top of the quencher removing a gas at a temperature of less than about 150° C, which gas still contains only small amounts of naphthalene, naphthoquinone and phthalic anhydride, scrubbing this gas with liquid naphthalene supplied to the top of a scrubber, from the bottom of the scrubber removing naphthalene containing small amounts of naphthoquinone and phthalic anhydride, feeding a minor proportion of the removed naphthalene to the quencher, cooling the major proportion of the removed naphthalene and recycling it for further scrubbing, and removing from the top of the scrubber a gas which is virtually free from naphthoquinone and phthalic anhydride.

2. The process according to claim 1, wherein the gas obtained from the oxidation of naphthalene is initially above about 280° C and is cooled in a pre-cooler to a temperature of not less than about 280° C.

3. The process according to claim 2, wherein the pre-cooling is effected by evaporative cooling.

4. The process according to claim 3, wherein pre-cooling is effected by evaporation of water.

5. The process according to claim 3, wherein pre-cooling is effected by evaporation of a high-boiling organic liquid.

6. The process according to claim 2, wherein the heat obtained in the pre-cooler is used to heat the feed gases for the oxidation of naphthalene.

7. The process according to claim 1, wherein the gas obtained from the oxidation of naphthalene is brought into contact in the quencher with liquid having a temperature of about 60° to 150° C.

8. The process according to claim 7, wherein the quenching liquid is recirculated in turbulent flow through a cooler in an amount such that the exit temperature of the liquid taken off from the quencher is at most about 150° C.

9. The process according to claim 8, wherein the temperature difference between the coolant and the quenching liquid is less than about 20° C.

10. The process according to claim 1, wherein the containers, coolers and pipes of the quenching system are made of stainless steel.

11. The process according to claim 1, wherein the material for the containers, coolers and pipes of the quenching system is made of steel and the surfaces which come into contact with the reaction products or condensation products are smoothed.

12. The process according to claim 11, wherein the smoothed surfaces of the quencher, the cooler and the pipes arre mechanically smoothed.

13. The process according to claim 11, wherein the surfaces of the quencher, cooler and pipes are smoothed by coating with plastic, enamel, ceramic or metal.

14. The process according to claim 1, wherein scrubbing of the gas taken off at the top of the quencher with naphthalene is effected in a counter-current.

15. The process according to claim 14, wherein the liquid product from the naphthalene scrub is pumped through a cooler wherein its temperature is brought to about 60° to 120° C prior to recycling for further use in scrubbing.

* * * * *